United States Patent [19]

Carr et al.

[11] Patent Number: 5,292,752
[45] Date of Patent: Mar. 8, 1994

[54] ANTITHROMBOTIC COMPOUNDS

[75] Inventors: Albert A. Carr; Richard C. Dage; John E. Koerner; Tung Li, all of Cincinnati; Francis P. Miller, Loveland; Thaddeus R. Nieduzak, Golf Manor, all of Ohio

[73] Assignee: Merrell Dow Pharmaceuticals Inc., Cincinnati, Ohio

[21] Appl. No.: 847,971

[22] Filed: Mar. 5, 1992

Related U.S. Application Data

[63] Continuation-in-part of Ser. No. 673,888, Mar. 22, 1991, abandoned, which is a continuation-in-part of Ser. No. 604,651, Nov. 1, 1990, abandoned, which is a continuation-in-part of Ser. No. 454,497, Dec. 21, 1989, abandoned.

[51] Int. Cl.$^5$ .................. A61K 31/445; C07D 211/32
[52] U.S. Cl. ..................................... 514/330; 514/821; 514/822; 546/225
[58] Field of Search ................ 546/225; 514/330, 821, 514/822

[56] References Cited

U.S. PATENT DOCUMENTS

| 4,783,471 | 11/1988 | Carr | 514/331 |
| 4,876,262 | 10/1989 | Oimuma et al. | 546/225 |
| 5,093,341 | 5/1992 | Carr | 546/225 |

FOREIGN PATENT DOCUMENTS

| 235752 | 9/1982 | European Pat. Off. | 546/225 |
| 320983 | 6/1989 | European Pat. Off. | 546/225 |

*Primary Examiner*—Richard L. Raymond
*Attorney, Agent, or Firm*—William R. Boudreaux; J. Michael Dixon

[57] ABSTRACT

The present invention is directed to a new class of piperidinyl medicinal agents which are useful as antithrombotic agents and as serotonin 5HT$_2$ antagonists.

15 Claims, No Drawings

ANTITHROMBOTIC COMPOUNDS

This is a continuation-in-part of application Ser. No. 07/673,888, filed Mar. 22, 1991, now abandoned which is a continuation in part of 07/604,651, filed Nov. 1, 1990, now abandoned which was a continuation-in-part of application Ser. No. 07/454,497, filed Dec. 21, 1989, now abandoned.

SUMMARY OF THE INVENTION

The present invention is directed to 1-(4-fluorophenyl)-2-[4-[(4-methanesulfonamidophenyl)carbonyl]-1-piperidinyl]ethanone and 1-(4-fluorophenyl)-2-[4-[(4-acetamidophenyl)carbonyl]-1-piperidinyl]-ethanone, their use as antithrombotic agents, their use as serotonin 5HT$_2$ antagonists, their use as D$_2$ antagonists and to their use as antiarrhythmic agents.

DESCRIPTION OF THE PRIOR ART

European Patent Application 0 235 752 discloses a class of sulfonamido-derivatives which can be described by the following formula:

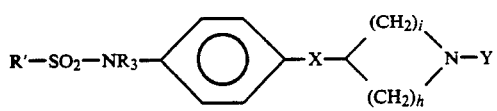

in which R' is lower alkyl or tolyl, R$_3$ is represented by lower alkyl, lower alkenyl, hydrogen, cycloalkyl, or cycloalkylalkyl; X is carbonyl, hydroxymethylene, or methylene; h and i are both integers from 1 to 3; and Y can be represented by hydrogen, lower alkyl, lower alkenyl, cyano, acetyl ester, or A-B, in which A is a straight chain alkylene bridging group containing from 1 to 5 carbon atoms which may be optionally substituted or unsaturated and B is selected from one of 28 aryl or heterocyclic moieties. Examples of these aryl and heterocyclic moieties include phenyl, naphthyl, thiophenyl, pyrimidinyl, pyrrolidinyl, quinolinyl, furanyl, pyrrolinyl, thiazolinyl, pyridinyl, indolinyl, etc. The European Application discloses that these compounds are antiarrhythmic agents.

This reference does not disclose the compounds, 1-(4-fluorophenyl)-2-[4-[(4-methanesulfonamidophenyl)carbonyl]-1-piperidinyl]-ethanone and 1-(4-fluorophenyl)-2-[4-[(4-acetamidophenyl)carbonyl]-1-piperidinyl]-ethanone.

European Patent Application 0 320 983 discloses some sulfonamido- and acetamido-derivatives of the formula:

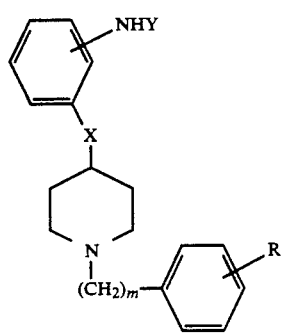

Formula I in which Y is represented by H, CO(CH$_2$)$_n$CH$_3$ in which n is an integer from 0-3, or SO$_2$(CH$_2$)$_n$CH$_3$ in which n is an integer from 0-3; X is represented by CO, CHOH, or C=N—O—A, wherein A is represented by hydrogen or a C$_{1-4}$ alkyl; R is either selected from the group consisting of halogens, lower alkyl groups, lower alkoxy groups, and hydrogen or R is a divalent substituent and is represented by a 3,4-methylenedioxy or a 3,4-ethylenedioxy group; m is an integer from 1-5. This application discloses that these compounds are antiarrhythmic agents, serotonin 5HT$_2$ antagonists, and that the compounds are useful in the treatment of thrombotic- and embolic- related illnesses.

This application's disclosure is limited to compounds in which there is an unsubstituted alkylene bridging group between the 1-position of the piperidinyl ring and the phenyl ring. This reference does not disclose any compounds in which a carbonyl group occupies this position. This application discloses neither 1-(4-fluorophenyl)-2-[4-[(4-methanesulfonamidophenyl)carbonyl]-1-piperidinyl]-ethanone nor 1-(4-fluorophenyl)-2-[4-[(4-acetamidophenyl)carbonyl]-1-piperidinyl]-ethanone.

BACKGROUND OF THE INVENTION

Each year nearly 1 million Americans suffer an acute myocardial infarction, approximately 20 percent of these individuals will die. Recent evidence has revealed that acute thrombosis plays an important role in most myocardial infarctions. In fact, it is estimated that acute thrombosis is the primary pathophysiological mechanism in 80-90% of acute transmural infarctions. Not surprisingly, recognition of the important role of thrombi and thus of platelet aggregation in myocardial infarction has intensified efforts to develop safe and effective antithrombotic agents.

A thrombus is an aggregation of blood factors, primarily platelets and fibrin with entrapment of other formed elements of the blood. Thrombi can also consist of primarily platelet aggregates. Thrombi are typically formed in order to prevent excessive bleeding from injured blood vessels. Thrombi are typically formed in the following manner.

The vascular endothelium serves as a barrier between the blood borne platelets which continually circulate throughout the body and the proaggregatory subendothelial components, which are primarily collagen. In addition to serving as a physical barrier, the cell membranes of the endothelial lining contain negatively charged components which serve to create an electrostatic repulsion between the platelets and the lining of the vessels. Trauma to the blood vessel will disrupt this endothelial lining and allow the platelets to come in contact with the underlying collagen and fibronectin. This causes the platelets to adhere to the subendothelial surface. This initial adherence causes the release, from these platelets, of a number of chemicals such as adenosine diphosphate, serotonin, and thromboxane A$_2$, all of which have a proaggregatory effect upon the initial platelet aggregate or plug and stimulate other circulating platelets to adhere to this newly formed plug. The additional adherence of these platelets stimulate the further release of these proaggregatory chemicals, which causes further growth of the platelet plug. Thus a self-perpetuating cycle is initiated which promotes the growth of the plug.

In addition to adhering to the injured vascular wall and forming aggregates, activated platelets accelerate the generation of thrombin which acts to convert the plasma protein, fibrinogen, into fibrin, thereby stabilizing the thrombus and promoting its growth. Prior to the conversion of fibrinogen into fibrin, a sequence of enzymatic conversions take place on the platelet surface which ultimately leads to the formation of fibrin. Both the negatively charged phospholipids on the platelet surface and calcium are essential for the maximal activation of Factor X. Once Factor X is activated, prothrombin is converted to thrombin which cleaves fibrinogen into fibrin and activates Factor XIII. This Factor catalyzes the crosslinking reaction of fibrin which stabilizes the platelet mass. In addition, thrombin is a powerful platelet activator and will act to perpetuate the process.

Thus once the platelets come in contact with the subendothelial surface, a reaction is initiated in which a number of positive feedback control systems act to produce a thrombus which blocks off the affected vasculature. The entire process (ie. platelet aggregation, fibrin generation, and polymerization) is referred to as hemostasis and is important in the prevention of excessive bleeding from the wound.

Although the formation of thrombi is desirable in a bleeding vessel, it is pathological in an intact vessel. Thrombi occur in intact vessels due to minor alterations in the endothelial cell surface or injuries that result in the disruption of the endothelial linings. Even relatively minor alterations can allow the platelets to come in contact with collagen and initiate the process described above. These minor alterations occur from a variety of causes. These causes include stasis, (ie. decreased movement of blood in the cardiac chambers or blood vessels) which induces damage due to lack of oxygen and reduces the shear forces that ordinarily discourage platelet interaction. Another cause is the damage which the process of atherosclerosis inflicts upon the endothelial linings. Endothelial linings are known to be disrupted at the site of atherosclerotic lesion.

Thus, a significant amount of research has been focused on finding drugs which will prevent the platelets from undergoing aggregation due to these minor alterations which are commonly found on the endothelial linings. Part of the research has been directed at exploring what effect could be achieved by administering an antagonist of serotonin, one of the proaggregatory substances which is released when the platelets initially begin to aggregate. Although serotonin is a relatively weak proaggregatory factor, it has been discovered that serotonin has a synergistic effect upon the primary proaggregatory clotting factor, ADP. Thus serotonin amplifies the proaggregatory effect of ADP.

Ketanserin is a serotonin antagonist. It reacts at the $5HT_2$ receptor. Bush et al reported this compound was extremely effective in preventing thrombus formation in canine models which have been designed to screen for this activity. *Drug Development Research, Vol.* 7, pages 319–340 (1986).

DETAILED DESCRIPTION OF THE INVENTION

In accordance with the present invention, it has been discovered that the serotonin $5HT_2$ antagonists, 1-(4-fluorophenyl)-2-[4-[(4-methanesulfonamidophenyl)carbonyl]-1-piperidinyl]-ethanone and 1-(4-fluorophenyl)-2-[4-[(4-acetamidophenyl)carbonyl]-1-piperidinyl]-ethanone, as well as their pharmaceutically acceptable acid addition salts, are effective in the prevention of acute thrombosis, especially those of the coronary arteries. These compounds decrease the rate at which platelets aggregate as the result of minor alterations in the endothelial lining of the vasculature and therefore prevent the formation of acute pathological thrombi. Since the compounds are serotonin $5HT_2$ antagonists, they are useful in the treatment of a number of disease states.

1-(4-Fluorophenyl)-2-[4-[(4-methanesulfonamidophenyl)carbonyl]-1-piperidinyl]-ethanone and 1-(4-fluorophenyl)-2-[4-[(4-acetamidophenyl)carbonyl]-1-piperidinyl]-ethanone can be represented by the following formula:

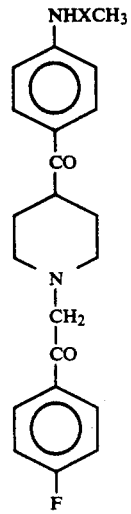

FORMULA I in which X is represented by CO or $SO_2$.

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such as methane sulfonic acid and 2-hydroxyethane sulfonic acid. Either the mono- or di-acid salts can be formed, and such salts can exist in either a hydrated or substantially anhydrous form. In general, the acid addition salts of these compounds are soluble in water and various hydrophilic organic solvents and which in comparison to their free base forms, generally demonstrate higher melting points.

The compounds of Formula I can be prepared using techniques well known in the art. One method of preparing these compounds is to carry out an N-alkylation between a 2-halo-4'-fluoro-acetophenone as described by Formula II in which Y is represented by a halogen atom, such as chlorine or bromine, and an acetamido- or methanesulfonamido-derivative as described by Formula III in which X is represented by CO or $SO_2$:

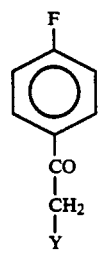

FORMULA II

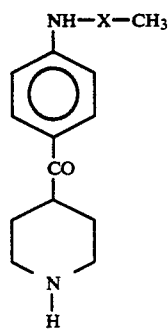

FORMULA III

As is apparent to those skilled in the art, X should be represented by CO in the compound of Formula III when an acetamido derivative is desired and X should be represented by $SO_2$ when a methanesulfonamido derivative is desired. The N-alkylation can be carried out in the following manner. Approximately equivalent amounts of the compounds of Formulae II and III are contacted in an appropriate solvent in the presence of a molar excess of a base such as sodium bicarbonate. The reaction can be optionally conducted in the presence of a catalyst such as tetrabutyl ammonium iodide. The reaction is typically carried out in a solvent such as a mixture of tetrahydrofuran/water, at a temperature range of from 25°–70° C. for a period of time ranging from about 0.5–24 hours.

The reaction is then quenched by the addition of brine, and the desired compound of Formula I is recovered by extraction with an organic solvent such as chloroform. The desired compound will be located in the organic phase. The organic phase is then typically dried and subjected to filtration and concentration in order to yield the crude compound of Formula I. The compound of Formula I can the be purified by recrystallization as is known in the art. 2-Butanone/cyclohexane or methanol/2-butanone are examples of suitable solvent systems for the recrystallization.

The acetophenones of Formula II are known in the art as are their methods of preparation. The piperidinyl derivatives of Formula III are also known in the art. European Patent Application 0 320 983 discloses methods for their preparation.

As noted above, the piperidinyl derivatives of Formula I are antithrombotic compounds. As used in this application the term "antithrombotic" should be construed as referring to the ability to either prevent or decrease the formation of acute pathological thrombi or emboli. It should not be construed as referring to the ability to dissolve a thrombus that has already formed. For the purpose of this application, the difference between a thrombus and an embolus, is that an embolus can be be an entire thrombus or a portion of a thrombus, that produces occlusion by moving to the site of occlusion from other parts of the circulation. It is not produced at the site of occlusion as is a thrombus.

One method of demonstrating the antithrombotic utility of these compounds is via the canine model of cyclic coronary blood flow reduction This procedure is well known in the art and has been described by John D. Folts, Edward B. Crowell Jr. and George G. Rowe, *Circulation* Vol 54, pages 365–370 (1976).

In Folts's model, the left anterior descending coronary artery of a canine is surgically isolated and the endothelial lining of this artery is purposefully damaged by squeezing the vessel in order to insure that the platelets will have the opportunity to come in contact with the collagen underlying the endothelial lining. This initiates the process of thrombus formation which was described above. An electronic flow probe is then placed on the artery so that blood flow through this vessel can be measured. A constrictor is then placed around the artery to produce a critical stenosis. The stenosis is said to be critical because the degree of stenosis is adjusted to abolish the hyperemic response following a 15 second occlusion of the artery. Shortly after producing the critical stenosis, blood flow through this segment of coronary artery will slowly decrease to near zero followed by a sudden return to control levels. The sudden decrease in blood flow is caused by the formation of a platelet thrombus which occludes the artery. The sudden return of blood flow is due to dislodgement of the thrombus and/or its resulting conversion into an emboli.

This model can be utilized to test compounds for the ability to inhibit platelet aggregation and therefore prevent the formation of thrombi. Canines who are pretreated with a compound having such an antithrombotic effect, will either not experience these decreases in blood flow (ie. cyclic flow reduction, CFR) or will experience significantly fewer of these episodes or will experience episodes of a smaller magnitude during the test period.

1-(4-Fluorophenyl)-2-[4-[(4-methanesulfonamidophenyl)carbonyl]-1-piperidinyl]-ethanone (Compound #1) and 1-(4-fluorophenyl)-2-[4-[(4-acetamidophenyl)carbonyl]-1-piperidinyl]-ethanone (Compound #2) were tested in this model. For comparative purposes, 1-(3-pyridyl)-2-[4-[(4-methanesulfonamidophenyl)carbonyl]-1-piperidinyl]-ethanone (Compound #3) was also tested in this model. This compound was prepared and described in Example 35 of European Patent Application 0 235 752, supra. The following results were obtained.

TABLE I

| COMPOUND | DOSAGE TO PREVENT CFR |
|---|---|
| Compound #1 | 0.001 mg/kg (iv) |
| Compound #2 | 0.001 mg/kg (iv) |
| Compound #3 | >0.1 mg/kg (iv)[1] |

[1]Ineffective At This Dose

Since the compounds are effective as antithrombotic agents, they can be utilized in a variety of clinical settings in which a patient is at risk of developing pathological acute thrombi. As noted above, they should be administered on a prophylactic basis to prevent the occurrence of an acute thrombotic episode, not to lyse thrombi which have already occurred.

For example, patients who have undergone thrombolysis with agents such as tissue plasminogen activator are at a high risk of suffering subsequent acute coronary artery thrombosis. The compounds of Formula I can be administered to these patients to prevent them from suffering additional acute coronary artery thrombotic episodes and any ensuing myocardial infarction.

They can also be used to decrease the time for re-establishing patent blood flow with thrombolysis, since they prevent acute thrombotic episodes. Acute thrombotic episodes routinely occur in patients undergoing thrombolysis and prolong the time required to re-establish patent blood flow. Patients who have undergone either a coronary bypass procedure or angioplasty are also typically at a greater risk of suffering thrombosis and thus can benefit from treatment as well. Other patients who will benefit from therapy include patients with saphenous vein bypass grafts, preventative therapy for acute occlusion after coronary angioplasty, secondary prevention of stroke recurrence, thrombosis of arteriovenous cannula in patients on hemodialysis and to prevent the occurrence of stroke and coronary thrombosis in patients with atrial fibrillation.

The compounds can also be administered to patients to prevent the occurrence of transient ischemic attacks (TIA). These attacks result from the formation of platelet emboli in severely atherosclerotic arteries, usually one of the carotid arteries, and these attacks are the forerunners of cerebral thrombus, i.e., stroke.

Thus these compounds can be used to prevent the occurrence of pathological acute thrombotic or embolic episodes. In order to achieve this result it is necessary that the compounds be administered to the patient in an antithrombotic quantity. The dosage range at which these compounds exhibit this antithrombotic effect can vary depending upon the particular compound being administered, the severity of the thrombotic episode, the patient, other underlying disease states the patient is suffering from, and other medications that may be concurrently administered to the patient. Generally though, these compounds will exhibit an antithrombotic effect at a dosage range of from about 0.001 mg/kg of patient body weight/day to about 4 mg/kg of patient body weight/day. The administration schedule will also vary widely, but will typically be from 1 to 4 times daily. The compounds can be administered by a variety of routes. They are effective if administered orally or parenterally.

If desired, the compounds can be administered in combination with other antiaggretory substances, such as, for example, aspirin (300-1200 mg/day), dipyridamole (300-400 mg/day), ticlopidine 50-500 mg/day), warfarin (25-300 mg/day), hirudin (0.1-100 mg/kg/day), or MDL 28,050. The compounds can also be administered in combination with a thromboxane synthetase inhibitor, such as, for example, ozagrel, dazmegrel, SQ 29,548, or SQ 30741. These thromboxane synthetase inhibitors are typically administered at a dosage range of from 0.5-50 mg/kg/day. The compounds of Formula I and the thromboxane synthetase inhibitors can be compounded into a single dosage form and administered as combination product. Methods for producing such dosage forms are well known in the art.

As used in this application:

a) the term "antithrombotic" should be construed as referring to the ability to either prevent the occurrence of or decrease the rate of occurrence of pathological acute thrombotic or embolic episodes;

b) the phrase "pathological acute thrombotic episodes" refers to the formation of a thrombus in an intact blood vessel, or to the obstruction of blood flow by an embolism, which has the potential of causing a myocardial or cerebral infarction, a stroke, a TIA, or other symptoms associated with an impairment of blood flow, and;

c) the phrase "treating thrombotic illness" should be construed as referring to the ability to either prevent the occurrence of or decrease the rate of occurrence of pathological acute thrombi or emboli.

As noted above, patients who have undergone angioplasty suffer a greater incidence of thrombosis. This has also been referred to as early restenosis and is due to platelet aggregration as described above. These patients also suffer from a condition which has been described as late restenosis which can occur weeks or months after angioplasty. This reocclusion is due to vacular smooth muscle cell hyperplasia. Platelet derived growth factor (PDGF) is believed to control the rate at which this proliferation occurs by stimulating the rate of DNA synthesis and mitosis in these cells. Vascular smooth muscle cell proliferation is also a key event in the pathogenesis of atherosclerosis. Araki et al reported that serotonin stimulates PDGF induced DNA synthesis. Atherosclerosis, 83 (1990) 29-34. Araki et al. reported that Ketanserin, a $5HT_2$ antagonist, inhibited PDGF induced DNA synthesis in a culture of rabbit vascular smooth muscle cells. Araki et al also reported that ketanserin inhibited phospholipase C mediated hydrolysis of phosphoinositides in rabbit vascular smooth muscle cells. Both of these in-vitro assays are models of anti-atherosclerotic activity. SCRIP reported that clinical trials are underway with ketanserin to confirm its beneficial effects in late restenosis. Oct. 19, 1990.

Since the compounds of Formula I are serotonin $5HT_2$ antagonists, they can be used in the treatment of late restenosis and to inhibit the development of atherosclerosis. The compounds inhibit the development vacular smooth muscle cell hyperplasia. They should be administered on a prophylactic basis to prevent the development of this condition. The dosage range at which these compounds inhibit PDGF induced vacular smooth muscle cell hyperplasia will be within the dosage range described below wherein these compounds exhibit their serotonin $5HT_2$ antagonist effects. The compounds will also exhibit an anti-atherosclerotic effect within these dosage ranges.

As noted above, the compounds are also serotonin $5HT_2$ antagonists The ability of the compounds to antagonize the effects of serotonin at the $5HT_2$ receptor can be demonstrated by the spiroperidol binding test as described by Peroutka et al., in Mol. Pharmacol., Vol. 16, pages 687-699 (1979). In this test, $5HT_2$ receptors are exposed to both [$^3$H] spiroperidol, (a substance known to have a specific affinity for the receptor) and the test compound. The extent to which there is a decrease in binding of the [$^3$H] spiroperidol to the receptor is indicative of the affinity of the test compound for the $5HT_2$ receptor.

1-(4-Fluorophenyl)-2-[4-[(4-methanesulfonamidophenyl)carbonyl]-1-piperidinyl]-ethanone (Compound #1) and 1-(4-fluorophenyl)-2-[4-[(4-acetamidophenyl)-carbonyl]-1-piperidinyl]-ethanone (Compound #2) were tested in this procedure. For comparative purposes, 1-(3-pyridyl)-2-[4 -[(4-methanesulfonamidophenyl)carbonyl]-1-piperidinyl]ethanone (Compound #3) and N-[4-[[1-[2-(4-fluoro phenyl)ethyl]-4-piperidne]carbenyl]phenyl] methane sulfononamide (compound #4) were also tested. Compound #4 was described in European Application 0 320 983, supra, as Example Number 8 and was prepared in that manner. The following results were obtained.

TABLE II

| Compound | $IC_{50}$ |
| --- | --- |
| Compound #1 | 78 nM |
| Compound #2 | 20 nM |
| Compound #3 | >5000 nM |
| Compound #4 | 100 nM |

The ability of the compounds to antagonize the $5HT_2$ receptor in vivo can be demonstrated via the 5-DMT head twitch test as described by Friedman et al. in *Commun. Psychopharmacol., Vol.* 3, pages 89–92, (1979). The administration of 5-methoxy-N,N-dimethyltryptamine (DMT) to mice typically produces a characteristic head twitch in the mice. In this test, the mice are administered 5-DMT and a test compound. An absence of head twitches in the mice is considered to be predictive of the ability of the test compound to antagonize the $5HT_2$ receptor in vivo. Table III reports the results which were obtained:

TABLE III

| Compound | $ED_{50}$ FOR ABOLITION OF HEAD TWITCH (mg/kg, ip) |
| --- | --- |
| Compound #1 | 0.034 |
| Compound #2 | 0.051 |
| Compound #3 | >200 |
| Compound #4 | 0.49 |

The dosage range at which these compounds exhibit their ability to block the effects of serotonin at the $5HT_2$ receptor can vary depending upon the particular compound being administered, the particular disease or condition being treated and its severity, the patient, other underlying disease states the patient is suffering from, and other medications that may be concurrently administered to the patient. Generally though, these compounds will exhibit their serotonin $5HT_2$ antagonist properties at a dosage range of from about 0.001 mg/kg of patient body weight/day to about 4.0 mg/kg of patient body weight/day. The compounds can be administered orally or parenterally to achieve these effects.

It has recently been reported that there are two subtypes of the serotonin $5HT_2$ receptor. These two subtypes have been referred to as the $5HT_{2A}$ and the $5HT_{2B}$ subtypes. McKenna et al., *Neuropharmacology, Vol.* 29, No. 3, pages 193–198 (1990) and Pierce et al., *Journal of Neurochemistry, Vo.* 52, No. 2, page 656 (1989). The compounds of Formula I have a higher affinity for the $5HT_{2A}$ receptor than for the $5HT_{2B}$ receptor. This affinity can be demonstrated by the methods of McKenna and Pierce.

Since the compounds are serotonin $5HT_2$ antagonists, they are useful in the treatment of a variety of disease states and conditions. The compounds of Formula I are useful in the treatment of anxiety, variant angina, anorexia nervosa, Raynaud's phenomenon, intermittent claudication and coronary or peripheral vasospasms. These conditions and diseases can be relieved by administering to a patient in need thereof, a compound of Formula I in an amount sufficient to treat the disease or condition (i.e., an anxiolytic amount, anti-anginal amount, anti-anorexic amount, etc.). This quantity will be within the dosage range at which the compounds exhibit their serotonin $5HT_2$ antagonistic properties.

The compounds of Formula I are also useful in the treatment of fibromyalgia. As used in this application, fibromyalgia refers to a chronic disease state wherein the patient suffers from numerous symptoms such as, for example, widespread generalized musculoskeletal pains, aching, fatigue, morning stiffness and a sleep disturbance which can be characterized as an inadequacy of stage 4 sleep. Administration of the compounds of Formula I in a anti-fibromyalgia amount relieves or alleviates the symptoms the patient is experiencing. An anti-fibromyalgia amount will be within the dosage range described above wherein these compounds exhibit their serotonin $5HT_2$ antagonist effects.

The compounds of Formula I can also be used to treat the extrapyramidal symptoms that often accompany the administration of neuroleptic agents such as haloperidol, chlorpromazine, etc. These extrapyramidal side effects (EPS) can manifest themselves in a variety of ways. Some patients experience a parkinsonian-like syndrome, wherein they experience muscular rigidity and tremors. Others experience akathisia, which can be characterized as a compelling need for the patient to be in constant movement. A few patients experience acute dystonic reactions, such as facial grimacing and torticollis.

The administration of a compound of Formula I to a patient in need thereof, in an anti-EPS amount, will relieve or alleviate the symptoms that the patient is experiencing. The amount of compound which produces this anti-EPS effect is an amount within the dosage range at which the compounds exhibit their serotonin $5HT_2$ antagonistic effects.

As noted above, the compounds are useful in the treatment of variant angina. Patients suffering from variant angina experience coronary vasospasms which produce the chest pains typically associated with angina. These vasospams typically occur while the patient is at rest. Patients suffering from stable angina experience these pains in response to the increased myocardial oxygen consumption associated with exercise, emotion, etc. Patients with stable angina typically have extensive coronary atherosclerosis.

Serotonin produces a biphasic response in normal coronary vessels (ie. those without significant atherosclerotic damage). Low concentrations of serotonin produce coronary dilation, whereas higher concentrations produce constriction. Patients suffering from variant angina have an abnormal response to serotonin and experience constriction at doses much lower than normal individuals. Therefore serotonin $5HT_2$ antagonists benefit these patients by blocking this abnormal response to serotonin.

McFadden et al. recently reported that patients with stable angina do not show a biphasic response to serotonin. Intracoronay infusion of serotonin induced constriction of the coronary vessels in these patients at all concentrations tested. The patients also experienced anginal attacks during these infusions. New England Journal of Medicine 1991; 324:648–654. Golino et al. also reported similar findings. New England Journal of Medicine 1991; 324:641–648. Golino et al. reported that ketanserin, a $5HT_2$ antagonist, blocked coronary vessel constriction in patients with stable angina. McFadmden et al. and Golino et al. stated that their findings suggest that serotonin, released after the intracoronary activation of platelets, contributes to or causes myocardial ischemia in patients with coronary artery disease.

Since the compounds of Formula I are serotonin $5HT_2$ antagonists, they are useful in the treatment of both variant angina and stable angina (anigna pectoris).

The compounds of Formula I can be used on a prophylactic basis to prevent the occurrence of angina or they can be administered to a patient experiencing an anginal attack to terminate that attack. The amount of compound which produces this anti-anginal effect is an amount within the dosage range at which the compounds exhibit their serotonin 5HT$_2$ antagonistic effects.

As used in this application:

a) the terms "anxiety, variant angina, anorexia nervosa, Raynaud's phenomenon, and coronary vasospasms" are used in the manner defined in the 27th Edition of Dorland's Illustrated Medical Dictionary;

b) the term "patient" refers to a warm-blooded animal, such as for example rats, mice, dogs, cats, guinea pigs, and primates such as humans, c) the term "treat" refers to either relieving or alleviating the patient's disease or condition, and;

d) the term "stable angina" should be considered to be synonymous with "angina pectoris" and is being used in the manner defined in the 13th Edition of the MERCK MANUAL.

The compounds of Formula I increase the duration of the action potential of myocardial tissue producing an increase in the refractory period of that tissue. Thus, under the classification system of Vaughan Williams these compounds exhibit a Class III antiarrhythmic activity.

The compounds of the present invention having Class III antiarrhythmic properties are useful for treating a variety of arrhythmic conditions of the heart. Representative examples of arrhythmic conditions which are amendable to treatment with the compounds of the present invention include supra ventricular arrhythmias such as atrial threatening ventricular arrhythmias such as ventricular tachycardia, or ventricular fibrillation. These compounds will also prevent recurrent episodes of the arrhythmias mentioned above.

The quantity of compound needed to either terminate an arrhythmic episode or prevent the occurrence of an arrhythmic episode (i.e., an antiarrhythmic quantity) will vary depending upon the route of administration, the patient, the severity of the patient's condition, the presence of other underlying disease states, and the particular compound utilized. However as a general guideline, if the compound is being administered orally, then it is preferably administered within a dosage range of from about 1.0 to about 400 mg/kg of patient body weight/day. Likewise, if the compound is being administered parenterally then it is preferably administered within a dosage range of from about 0.1 to about 40 mg/kg of patient body weight/day. The patient's response to the compound can be monitored via an EKG or any other technique conventionally used in the art.

As used in this application:

a) the term arrhythmia refers to any variation from the normal rhythm of the heart beat, and;

b) the term antiarrhythmic refers to a compound capable of either preventing or alleviating an arrhythmia.

The compounds of Formula I will offer significant clinical advantages over the class III antiarrhythmics currently available. These compounds exhibit anixolytic, antithrombitic, as well as antiarrhythmic activity. Myocardial ischemia and anxiety can have major roles in the etiology of cardiac arrhythmias. Thus the compounds of Formula I will help to prevent the occurrence of arrhythmias caused by either ischemia or anxiety as well as controlling any arrhythmia that does occur regardless of its etiology.

The compounds of Formula I are also dopamine antagonists. They antagonize the effects of dopamine at the D$_2$ receptor. This antagonism can be demonstrated by the method of Creese et al., *European Journal of Pharmacology*, Vol. 46, page 377 (1977). Since the compounds are dopamine antagonists they will be effective in the treatment of psychotic illnesses such as schizophrenia, mania, etc. It is envisioned that they will be useful for the treatment of any medical condition for which known dopamine antagonists such as haloperidol or thioridazine are used. Since the compounds are also serotonin 5HT$_2$ antagonists, it is envisioned that they will have a lower incidence of extrapyraimidal side effects than other known dopamine antagonists that are available to clinicians, such as thioridazine, haloperidol, etc.

In order to exhibit these anti-psychotic properties, the compounds need to be administered in a quantity sufficient to antagonize the effect which dopamine has upon dopamine receptors. The dosage range at which these compounds exhibit this antagonistic effect can vary widely depending upon the particular disease being treated, the severity of the patient's disease, the patient, the particular compound being administered, the route of administration, and the presence of other underlying disease states within the patient, etc. Typically the compounds exhibit their antipsychotic effects at a dosage range of from about 0.01 mg/kg/day to about 25 mg/kg/day. Repetitive daily administration may be desirable and will vary according to the conditions outlined above. Typically, the compounds will be administered from 1–4 times daily.

As used in this application:

a) the term "psychosis" refers to a condition where the patient, e.g., a human, experiences a major mental disorder of organic and/or emotional origin characterized by derangement of the personality and loss of contact with reality, often with delusions, hallucinations or illusions. Representative examples of psychotic illnesses which can be treated with the compounds of the present invention include schizophrenia, and mania.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula I can be tableted with conventional tablet bases such as lactose, sucrose, and cornstarch in combination with binders, such as acacia, cornstarch, or gelatin, disintegrating agents such as potato starch or algenic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc. as are known in the art.

The compounds of Formula I may be admixed with any inert carrier and utilized in laboratory assays in order to determine the concentration of the compounds within the urine, serum, etc. of the patient as is known in the art.

The following examples are presented in order to further illustrate the present invention. However, they should not be construed as limiting the scope of the invention in any manner.

EXAMPLE I

The purpose of this example is to demonstrate a manner of preparing a piperidinyl derivative of Formula III, in which X is represented by CO.

33.9 g of N-phenyl-acetamide (251 mmol) was admixed with 45 g of $AlCl_3$ (338 mmol). This mixture was placed in a 5 liter round bottom flask, mechanically stirred and heated with steam until a dark viscous solution was obtained.

To this solution was added consecutively 46.0g of 4-chloro-carbonyl piperidine hydrochloride (250 mmol) and 90 g of $AlCl_3$ (675 mmol). This produced a dark red paste.

The paste was heated with steam for 15 minutes and then 100 ml of 1,1,2,2-tetrachloroethane was added which produced a translucent red solution. This solution was then heated for an additional 10 minutes.

The steam bath was then removed and the reaction was quenched by the slow addition of 2 kg of cracked ice. The solution was made basic with a 50% NaOH solution. This cold aqueous solution was then washed twice with toluene, and extracted twice with chloroform. The combined chloroform extracts were dried over $MgSO_4$ and evaporated to yield a yellow solid. The solid was washed in refluxing ethyl acetate at 76° C. and filtered to afford N-[4-(4-piperidinylcarbonyl)-phenyl]-acetamide as a light yellow solid.

A portion of this product was then converted into a hydrochloride acid addition salt in the following manner.

To 30 ml of stirred methanol under argon at 0° C. was added acetyl chloride (0.95 ml, 0.86 g, 13.4 mmol) dropwise with a syringe. This solution was then added dropwise to 3.0 g of the N-[4-(4-piperidinyl-carbonyl)-phenyl]-acetamide (12.2 mmol, prepared above) which had been dissolved in 50 ml of methanol.

This solution was then heated to reflux and diluted with 100 ml of refluxing ethanol. This solution was then concentrated to a volume of 75 ml.

The solution was cooled to room temperature which caused the precipitation of the intermediate N-[4-(4-piperidinylcarbonyl)phenyl]-acetamide as the monohydrochloride salt, m.p. 285° C.

EXAMPLE II

The purpose of this example is to demonstrate the preparation of 1-(4-fluorophenyl)-2-[4-[(4-acetamidophenyl)carbonyl]-1-piperidinyl]-ethanone (i.e., a compound of Formula I in which X is CO.)

To a solution of 3.0g (12.2 mmol) of N-[4-(4-piperidinyl-carbonyl)phenyl]-acetamide in 10 ml of water and 100 ml of tetrahydrofuran was added 2.3 g (13.4 mmol) of 2-chloro-4'-fluoro-acetophenone followed by 2.0g (24.4 mmol) of sodium bicarbonate. This mixture was heated to reflux for 1.5 hours. The reaction mixture was poured into 500 ml of brine and extracted with chloroform. The organic layer was dried with magnesium sulfate, filtered and concentrated to yield a solid which was recrystallized from 2-butanone/cyclohexane. 1-(4-Fluorophenyl)-2-[4-[(4-acetamidophenyl)carbonyl]-1-piperidinyl]-ethanone was obtained as an off-white solid having a mp of 168°–170° C.

EXAMPLE III

The purpose of this example is to demonstrate a manner of preparing a compound of Formula III in which X is represented by $SO_2$.

42.8 g of N-phenyl methanesulfonamide (250 mmol) was admixed with 45 g of $AlCl_3$ (338 mmol) in a 5 liter round bottom flask and heated with steam while being mechanically stirred. A dark viscous solution was obtained.

This solution was mixed with 46.0 g of 4-chlorocarbonyl piperidine hydrochloride (250 mmol) and 90.0 g of $AlCl_3$ (675 mmol) which produced a dark brown sludge.

1,1,2,2-Tetrachloroethane (100 ml) was added and the admixture was heated for an additional 15 minutes.

Heating was discontinued and the reaction was quenched by the addition of 4 kg of cracked ice. A gray precipitate was obtained.

The precipitate was recovered by filtration. The resulting solid was washed consecutively with water and ethyl ether and then air dried.

The resulting solid was dissolved in hot water, admixed with activated charcoal and filtered. The solution was then cooled to approximately 22° C. at which point the desired product precipitated from solution.

The solid material was filtered and dried to give N-[4-(4-piperidinyl-carbonyl)phenyl]-methanesulfonamide monohydrochloride which had a melting point of 303°–305° C.

EXAMPLE IV

The purpose of this Example is to demonstrate the preparation of 1-(4-fluorophenyl)-2-[4-[(4-methanesulfonamidophenyl)carbonyl]-1-piperidinyl]-ethanone (i.e., a compound of Formula I in which X is $SO_2$).

To a solution of 2.0g (6.3 mmol) of N-[4-(4-piperidinylcarbonyl)phenyl]-methanesulfonamide monohydrochloride in 10 ml of water and 100 ml of tetrahydrofuran was added 1.3 g (7.5 mmol) of 2-chloro-4'-fluoro-acetophenone followed by 1.3 g (15.7 mmol) of sodium bicarbonate and a catalytic amount of tertrabutylammonium iodide. This mixture was heated to reflux for approximately one hour. The reaction mixture was poured into 500 ml of brine and extracted with chloroform. The organic layer was dried with magnesium sulfate, filtered and concentrated to deliver a thick oil. Treatment of the oil with methanolic hydrogen chloride yielded a solid which was recrystallized from methanol/2-butanone. The resulting hydrochloride salt of 1-(4-fluorophenyl)-2-[4-[(4-methanesulfonamidophenyl)carbonyl]-1-piperidinyl]-ethanone was obtained as a white solid having a mp of 233°–7° C.

What is claimed is:

1. A compound of the formula:

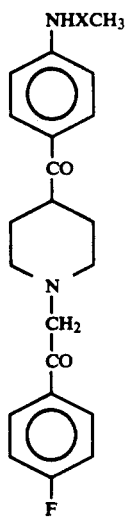

FORMULA I in which X is represented by CO or SO₂ and the pharmaceutically acceptable acid addition salts thereof.

2. A compound according to claim 1 wherein X is CO.

3. A compound according to claim 1 wherein X is represented by SO₂.

4. A pharmaceutical composition comprising a compound according to claim 1, present in an effective amount, in admixture with a pharmaceutically acceptable carrier.

5. A composition according to claim 4 which contains a thromboxane synthetase inhibitor.

6. A pharmaceutical composition comprising a compound according to claim 3, present in an effective amount, in admixture with a pharmaceutically acceptable carrier.

7. A method for the treatment of serotonin induced thrombotic illness caused by comprising the administration of a compound according to claim 1 in an anti-thrombotic amount to a patient in need thereof.

8. A method for the treatment of serotonin induced angina comprising administering to a patient in need thereof an anti-anginal amount of a compound according to claim 1.

9. A method for the treatment of serotonin induced anorexia nervosa comprising administering to a patient in need thereof an anti-anorexic amount of a compound according to claim 1.

10. A method for the treatment of serotonin induced Raynaud's phenomenon comprising administering to a patient in need thereof a compound according to claim 1 in an amount sufficient to relieve or alleviate the patient's symptomatology.

11. A method for the treatment of serotonin induced coronary vasospasms comprising administering to a patient in need thereof an anti-spasmodic amount of a compound according to claim 1.

12. A method for the treatment of serotonin induced fibromyalgia comprising administering to a patient in need thereof an anti-fibromyalgia amount of a compound according to claim 1.

13. A method for the treatment of serotonin induced extra-pyramidal side effects associated with neuroleptic therapy comprising amount of a compound according to claim 1.

14. A method for relieving or alleviating serotonin induced anxiety comprising administering to a patient in need thereof, an anxiolytic amount of a compound according to claim 1.

15. A method for the treatment of serotonin induced late restonosis comprising administering a compound according to claim 1 to a patient in need thereof.

* * * * *